United States Patent [19]

Clough et al.

[11] Patent Number: 5,366,863

[45] Date of Patent: Nov. 22, 1994

[54] TOTAL GONADOTROPAL ALPHA PEPTIDE CHAIN ASSAY

[75] Inventors: Kathleen M. Clough, Acton; Francis X. Cole, Stow, both of Mass.

[73] Assignee: Hygeia Sciences, Inc., Newton, Mass.

[21] Appl. No.: 505,307

[22] Filed: Apr. 5, 1990

[51] Int. Cl.$^5$ .................. C12Q 1/00; G01N 33/53; C07K 17/00

[52] U.S. Cl. .................. 435/7.1; 435/7.94; 435/7.92; 435/4; 435/28; 436/510; 436/814; 436/818; 436/916; 436/65; 530/313; 530/388.24

[58] Field of Search ............ 435/7.94, 28, 188, 805, 435/810, 7.92, 4, 7.1; 436/510, 814, 818, 906, 65; 514/12; 530/313, 388.24

[56] References Cited

U.S. PATENT DOCUMENTS

| | | | |
|---|---|---|---|
| 4,196,123 | 4/1980 | Rosemberg | 514/12 |
| 4,514,505 | 4/1985 | Caufield et al. | 436/500 |
| 4,659,678 | 4/1987 | Forrest et al. | 436/512 |

FOREIGN PATENT DOCUMENTS

WOA8304312 12/1983 European Pat. Off. .

OTHER PUBLICATIONS

Biological Abstracts, vol. 88, No. 1, 1989, Philadelphia, Pa., US; abstract No. 118277; M. S. Balin et al. 'Evaluation of the human gonadtroph free alpha–subunit secretory pools by administration of gonadotropin hormone-releasing hormone into normal subjects at different phases of the ovarian cycle.' p. AB–338 *abstract* J. Endocrinol. Invest., vol. 12, No. 6, 1989, pp. 373–382.

Biological Abstracts, vol. 88, No. 5, 1989, Philadelphia, Pa., US; abstract No. 48241, C. Rivier et al. "Immunoneutralization of endogenous inhibin modifies hormone secretion and ovulation rate in the rate." p. AB–337; *abstract* & Endocrinology vol. 125, No. 1, 1989, pp. 152–157.

*Primary Examiner*—Margaret Parr
*Assistant Examiner*—Bradley L. Sisson
*Attorney, Agent, or Firm*—Staas & Halsey

[57] ABSTRACT

An assay procedure for predicting the onset of the ovulation in a human subject. Urine samples are obtained on consecutive days and assayed for total gonadotropal alpha peptide chain content. The alpha chain content surges to indicate ovulation and the onset of the fertile period.

7 Claims, 3 Drawing Sheets

TOTAL α STANDARD CURVE

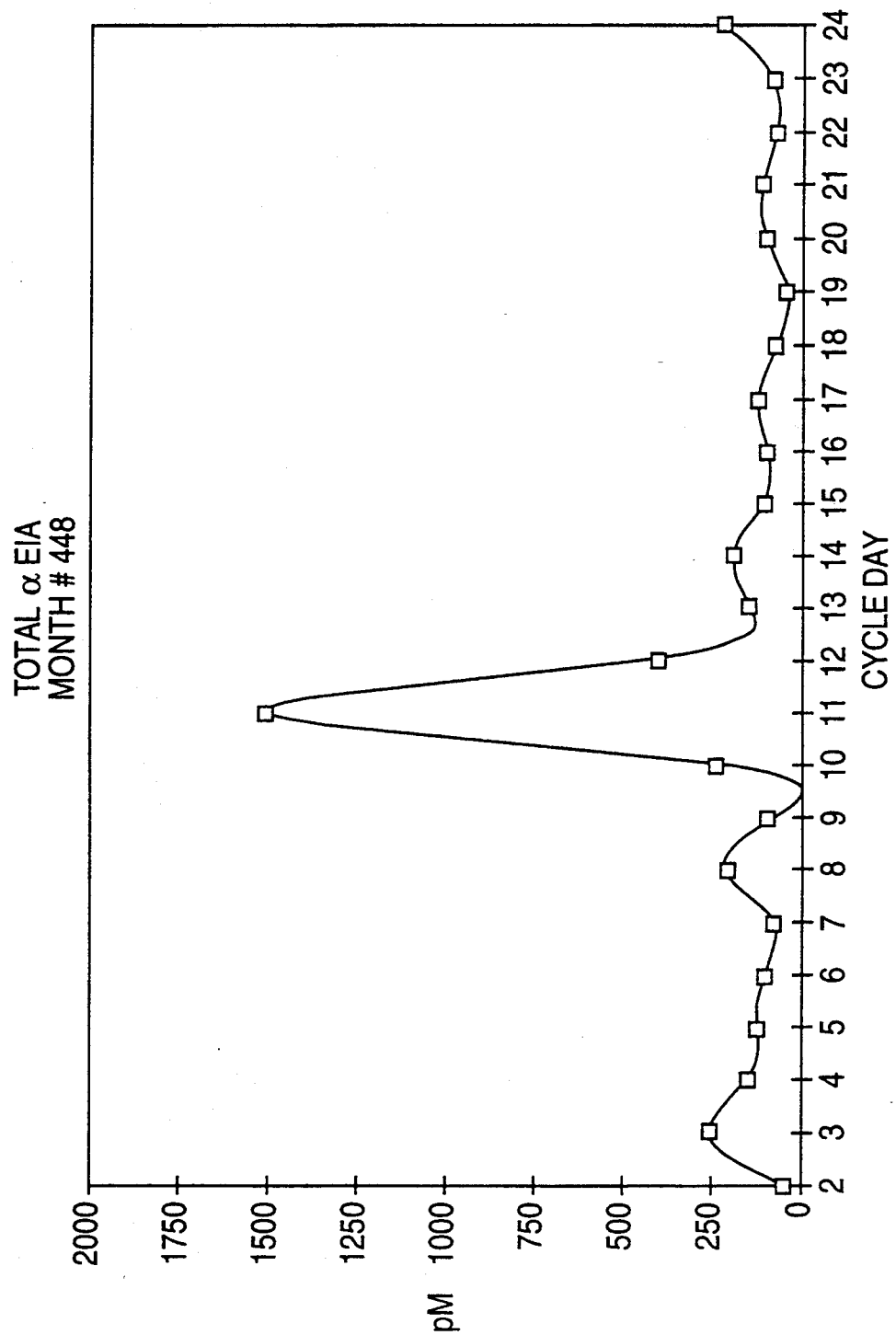

TOTAL GONADOTROPAL ALPHA PEPTIDE CHAIN ASSAY

BACKGROUND OF THE INVENTION

1. Field of the Invention

The present invention relates to assays for determining and/or detecting hormones in mammalian body fluids and in particular to assays for determining and/or detecting the luteinizing hormone surge which results in rupture of the preovulatory follicle and release of the ovum at ovulation. More particularly, the invention relates to the use of total gonadotropal alpha peptide chain content in urine as an enhanced indicator of luteinizing hormone content. Even more particularly, the invention relates to an immunoassay suitable for testing for constituents in human urine to determine the human fertile period, that is, the period in which viable sperm and a viable ovum may be present simultaneously in the female reproductive tract.

2. The Prior Art Background

For a number of reasons it may be clinically and/or diagnostically desirable to determine the presence and/or concentration of constituents in mammalian body fluids such as blood serum or urine. In some instances, mammalian hormonal activity and/or metabolism create situations where surges in concentrations of hormones or metabolites in body fluids may be chronologically related to other events. In particular, a surge in the concentration of luteinizing hormones (LH) in human urine may be used to ascertain the fertile period of the menstrual cycle. For couples experiencing difficulty in conceiving there is a need for identifying the optimum period for intercourse or artificial insemination.

The human menstrual cycle is governed by the cyclical release of hormones from the female glands and organs. Such release is predictable and specifically related to ovulation by which ova are released from the ovaries and the lining of the uterus is made ready for pregnancy. Eventually, the released hormones and/or metabolites thereof find their way into the urine. The specific biological phenomena are described in detail in a published dissertation of Kevin J. Catt and John G. Pierce entitled "Gonadotropic Hormones of the Adenohypophysis", which appears as Chapter 3 (pp 75-114) of a treatise of Yen, S. S. C. and Jaffee, R. B., REPRODUCTIVE ENDOCRINOLOGY, 2d ed., W. B. Saunders, Philadelphia (1978). And suffice it to say, that during a normal menstrual cycle, the level of LH in female serum surges to cause the preovulatory follicle to rupture and release the ovum. This process is known as ovulation. The LH surge may be detected in female urine approximately 8 to 24 hours after the surge occurs in the blood. The surge of LH in human urine has thus been used as an indication that the fertile period is ongoing or about to occur and a number of commercial assays for detecting the fertile period have been based on the measurement of LH concentrations in human urine.

Gonadotropins such as LH, follicle-stimulating hormone (FSH), human chorionic gonadotropin (hCG) and thyroid-stimulating hormone (TSH) are all well known hormones as discussed in the Catt et al. dissertation identified above. These hormones are all formed from two peptide chains (an alpha chain and a beta chain) which are non-covalently joined to present the intact hormone. The chains are capable of existing separately; however, they must be joined together to create a biologically active hormone. The alpha chains of LH, FSH, hCG and TSH are essentially identical but the beta chains are all different.

As is known in the art, the intact (holo) hormones and the free alpha and beta chains may be distinguished and assayed separately using various combinations of antibodies to private, public and/or conformational epitopes. In this regard, a public epitope is one that is accessible without regard to whether the chain is free or combined, a private epitope is one that is accessible only on free chains and a conformational epitope is one that is not available on either chain alone but only on an intact hormone. And, as indicated above, commercial fertile period assays have previously been configured to determine the LH surge by assaying for the intact hormone.

It has also been recognized that LH assays could potentially be directed to either total or free LH beta chain. However, there has been no suggestion in the prior art that there might be a sufficient correlation between preovulatory total alpha chain content and intact LH surges in urine to base a fertile period assay on total alpha chain. Even more so there has been no suggestion in the prior art that total alpha chain not only surges contemporaneously with LH but surges to a much greater level so that the assay is much more sensitive and precise.

SUMMARY OF THE INVENTION

In accordance with the invention it has been discovered that in the urine of normal cycling women the total content of gonadotropal alpha peptide chains in urine is considerably greater than the total LH beta chain or intact LH hormone content. It has also been discovered that the levels of alpha chain, beta chain and holohormone all increase in a coordinated fashion at mid cycle. Thus, it has been observed, in accordance with the invention, that the preovulatory surge of the holohormone is accompanied by a simultaneous magnified surge in total alpha chain. This facilitates construction of an assay having an enhanced signal to noise ratio compared to other assays based on the holohormone or on free or total beta chain. Measurements have shown that the molar equivalent concentration of gonadotropal alpha chain at the mid cycle surge is approximately five to ten times greater than the molar equivalent concentrations of the holohormone or the beta chain.

To take advantage of the foregoing observed phenomena, the invention provides an assay procedure which includes the steps of obtaining a sample of body fluid from a mammal and analyzing said sample to determine or detect gonadotropal alpha peptide chains without regard to whether the latter are free or part of an intact hormone. In another aspect of the invention, an assay procedure is provided for determining preovulatory surging of luteinizing hormone which includes the steps of obtaining a plurality of samples of body fluid from a host and comparing the total gonadotropal alpha peptide chain content of said samples. In yet a further more specific aspect of the invention, an assay procedure is provided for predicting the onset of ovulation in a human subject which comprises obtaining a urine sample from a host on each of a plurality of consecutive time periods, analyzing each of said samples to determine total gonadotropal alpha peptide chain content thereof, and observing a surge in said total gonadotropal alpha peptide chain content as a prelude to ovulation.

In the more specific aspects of the invention an assay procedure is provided wherein the samples are analyzed using an immunological procedure. The immunological procedure may include the step of forming a sandwich using two different antibodies, each of said antibodies being specifically bindable to a respective different binding site on the alpha chain.

In a preferred form of the invention, the assay procedure may include a sandwich ELISA procedure. And in a particularly preferred form of the invention, the samples are obtained on consecutive days and comprise first morning urine samples.

BRIEF DESCRIPTION OF THE DRAWINGS FIG. 1 is a chart which compares the mid cycle preovulatory surges of intact LH and total alpha chain on consecutive days of 7 cycles;

FIG. 2 is a standard curve relating total alpha chain content to spectrophotometric absorbance values; and FIG. 3 illustrates the total alpha content of urine during essentially an entire menstrual cycle.

DETAILED DESCRIPTION OF THE INVENTION

Figure 1:
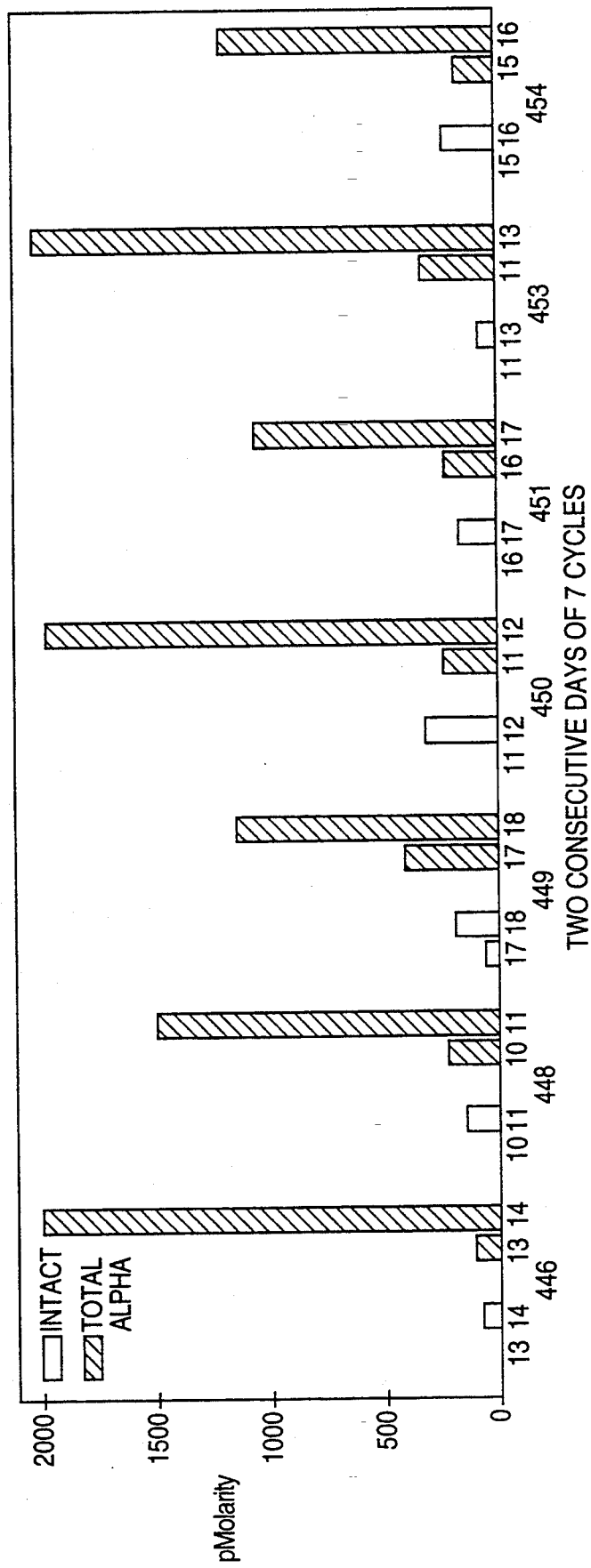

As set forth above, the present invention is based on the discovery of the occurrence of two unexpected phenomena during the menstrual cycle of normally cycling women. First it was discovered that the traditional mid cycle surge of intact LH in the system that triggers ovulation is accompanied by a contemporaneous surge in the total level of gonadotropal alpha peptide chains in the system. Additionally it has been discovered that the alpha chain surge is greatly magnified relative to the surge of the holohormone.

These phenomena were discovered by conducting dot blot analyses to determine the epitope specificity of certain LH antibodies. The antibodies investigated were HK1 2G9, LH25 2B10, INN-132, INN-72, LH26-2G9, WSP-2G5 and WSP-2B6. The INN antibodies are commercially available from I.D.C. (A-6080 Innsbruck-/IGLS, Gsturnsteig 10, AUSTRIA) and the WSP antibodies are available commercially from Western States Plasma (3887 Alta Vista Drive, Fallbrook, Calif.). The other antibodies are available in-house at Hygeia Sciences, Inc.

LH antigens (free beta chain, free alpha chain and intact holohormone; obtained from Scripps) were bound to nitrocellulose at a concentration of 5 $\mu$g/ml in 0.2M carbonate buffer (pH 8.0) via a 96-well device (Bio-Rad, Richmond, Calif.) by gravity filtration. The nitrocellulose was then exposed to a solution of 2% BSA in 0.2M Carbonate, pH 9.0 to block remaining binding sites. The monoclonal LH antibodies at a concentration of 25 $\mu$g/ml, 100 $\mu$L/well were gravity filtered through a membrane. Unbound antibody was removed by washing the wells three times with 300 $\mu$L of 0.2M Carbonate with 0.1% Tween 20 using vacuum filtration. Anti-mouse IgG labelled with Alkaline Phosphatase (Sigma Chemical, St. Louis, Mo.) diluted 1:1200 in blocking buffer, 100 $\mu$L/well, was gravity filtered, followed by three washes using the above mentioned wash buffer and vacuum filtration. A final wash with distilled water was used to remove any residual tween. The membrane was removed from the device and exposed to substrate consisting of 0.01% Nitro Blue Tetrazolium, 0.004M $CaCl_2$, and 0.5 mg/mL Indoxyl Phosphate in Veronal-Acetate Buffer, pH 9.6.

The results obtained were straight forward with very little background and it was determined that HK1 2G9 antibody is specific for a public epitope on the LH beta chain, LH25 2B10 antibody is specific for a public epitope on the LH beta chain, INN-132 antibody is specific for a public epitope on the alpha chain, INN-72 antibody is specific for a private epitope on the alpha chain, LH26-2G9 antibody is specific for a private epitope on the beta chain, WSP-2G5 antibody is specific for a public epitope on the alpha chain, and WSP-2B6 antibody is specific for a conformational epitope on the holohormone.

Pairs of these antibodies were thus used to develop sandwich ELISA assays for specific analytes. For example, WSP-2B6 (holohormone) and WSP-2G5 (alpha) could be used to assay for the intact hormone; INN-132 (alpha) and WSP-2G5 (alpha) could be used to assay for total alpha chain; and LH25 2B10 (beta) and HK1 2G9 (beta) could be used to assay for total beta chain.

Immunoassays were conducted using the foregoing pairs of antibodies and a 96 well Immulon plate. WSP-2B6, INN-132 and LH25 2B10 antibodies were used as the respective capture antibodies and the other antibody of each pair was labelled with horse radish peroxidase (HRP). The capture antibodies were dispersed in 0.05M PBS (pH 7.35) at different concentrations. The concentration of the WSP 2B6 antibody was 10 $\mu$g/ml; the concentration of the INN-132 antibody was 5 $\mu$g/ml; and the concentration of the LH25 2B10 antibody was 1 $\mu$g/ml. Each of these dispersions was coated (100 $\mu$l) in a plurality of wells and incubated overnight at room temperature.

For blocking, the plates were decanted and the wells were filled with 0.1M Tris pH 8.0 containing 2% BSA and 20% Sucrose and incubated for at least 30 minutes. Prior to use the blocking solution was decanted and the plate was rinsed with tap water. For long term storage, the blocking solution could be decanted and the plate tapped several times onto paper towels to remove residual liquid and then placed in a vacuum desiccator.

The HRP labelled WSP-2G5 antibody was dispersed in 0.1M Tris (pH 8.0) containing 1% bovine serum albumin (BSA), 1% polyethylene glycol (PEG-8000), and 0.1% Tween 20 at a concentration of 1 $\mu$g/ml, and the HRP labelled HK1 2G9 was dispersed at a concentration of 0.5 $\mu$g/ml. Urine samples were diluted 1:2 or greater in 0.1M TRIS, 1% BSA.

Figure 2:
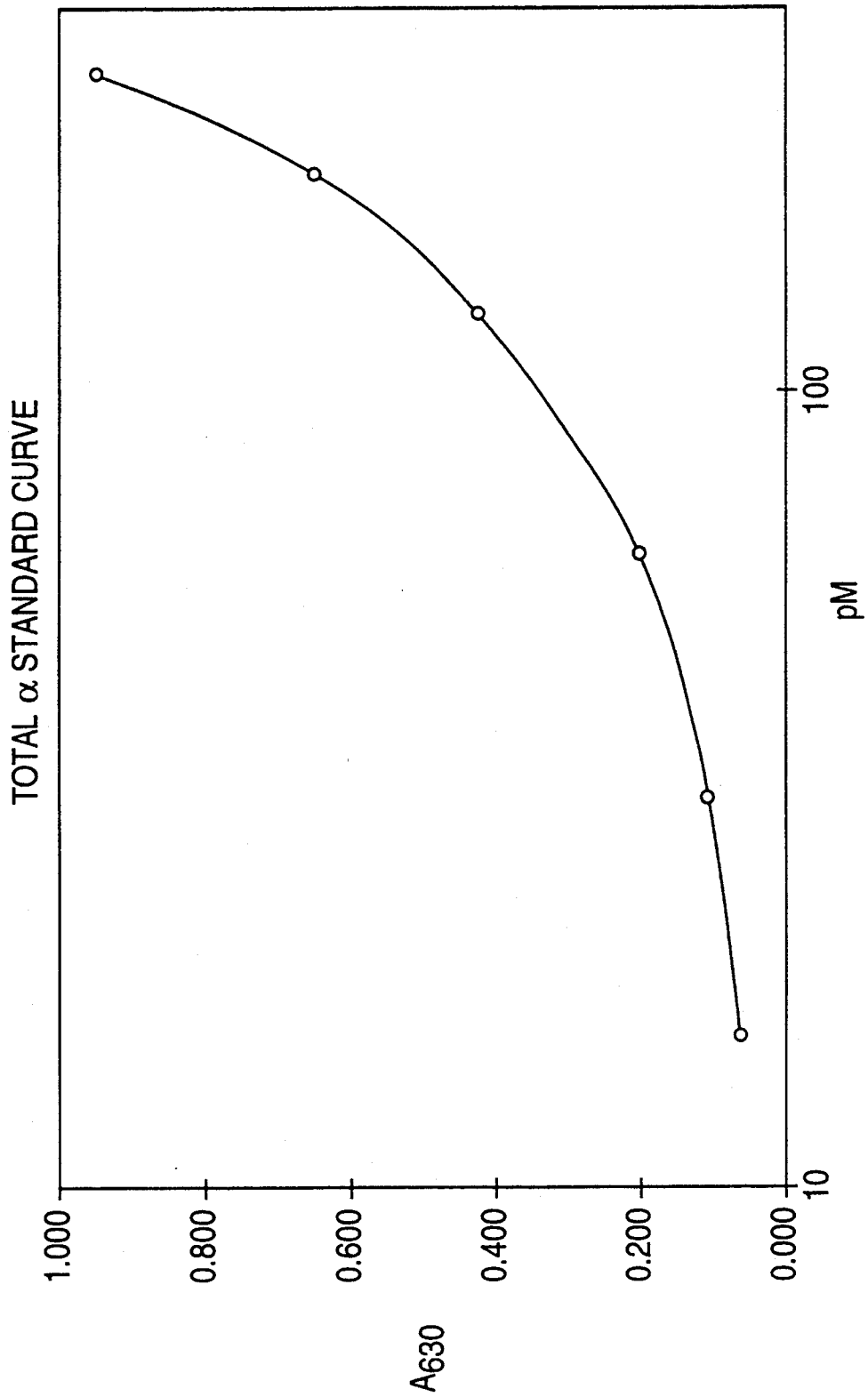

The assays were conducted using 50 $\mu$l of diluted sample and 50 $\mu$l of HRP labelled antibody dispersion. Incubation was allowed to proceed for one hour at room temperature and then the plates were decanted and washed 6 to 8 times. Color was developed using 100 $\mu$l of TMB substrate solution. The intensity of the color was detected on a spectrophotometric plate at absorbance 630 and results were evaluated using standard curves similar to the one presented in FIG. 2. The results for seven different panelists are set forth in Table I below and are summarized in FIG. 1. The data of Table I is set forth in terms of pica molar concentrations. From Table I and FIG. 1 it can be seen that total alpha chain content surges contemporaneously with the surge of intact LH and that the total alpha chain surge is much greater than the surges of other components.

| SURGE COMPARISON | | | | |
| --- | --- | --- | --- | --- |
| Cycle Day | LH Intact | Total Beta | Total Alpha | Free Alpha |
| Panelist #446 | | | | |
| 12 | 0 | 0 | 106 | 0 |
| 13 | 0 | 0 | 114 | 0 |
| 14 | 75 | 121 | 1995 | 702 |
| 15 | 0 | 0 | 387 | 99 |
| 16 | 0 | 41 | 212 | — |
| Panelist #448 | | | | |
| 9 | 0 | 0 | 88 | — |
| 10 | 0 | 37 | 242 | 46 |
| 11 | 138 | 112 | 1510 | 314 |
| 12 | 41 | 142 | 397 | 99 |
| 13 | 0 | 91 | 150 | 36 |
| Panelist #449 | | | | |
| 10 | 0 | 0 | 176 | — |
| 14 | 0 | 0 | 140 | — |
| 15 | 0 | 0 | 254 | — |
| 16 | 0 | 45 | 350 | 107 |
| 17 | 55 | 49 | 398 | 127 |
| 18 | 184 | 169 | 1135 | 250 |
| Panelist #450 | | | | |
| 10 | 0 | 34 | 326 | 119 |
| 11 | 0 | 53 | 220 | 101 |
| 12 | 300 | 253 | 1970 | 667 |
| 13 | 146 | 161 | 1400 | — |
| 14 | 76 | 331 | 496 | 371 |
| Panelist #451 | | | | |
| 15 | — | — | 119 | 0 |
| 16 | 0 | 0 | 219 | 32 |
| 17 | 162 | 116 | 1055 | 198 |
| 18 | 0 | 49 | 203 | 42 |
| 19 | 0 | 236 | 290 | 57 |
| Panelist #453 | | | | |
| 10 | 0 | 0 | 179 | — |
| 11 | 0 | 0 | 312 | 64 |
| 13 | 68 | 95 | 2010 | 496 |
| 14 | 0 | 0 | 364 | 33 |
| 15 | 0 | 199 | 535 | — |
| Panelist #454 | | | | |
| 14 | 0 | 55 | 347 | — |
| 15 | 0 | 0 | 149 | 54 |
| 16 | 207 | 172 | 1185 | 209 |
| 17 | 230 | 284 | 1062 | 159 |
| 18 | 88 | 376 | 468 | 111 |

The foregoing results are convincing and strongly prove that a fertile period assay may be based on an assay for total alpha chain. Such an assay is described in Example I hereinbelow.

EXAMPLE I

Total Alpha Chain Assay

Buffers
1. 0.1M Tris, pH 8.0 with 1% Bovine Serum Albumin (BSA). This buffer is used to prepare alpha chain standards and as a diluent for the urine sample.
2. 0.1M Tris, pH 8.0 with 1% BSA, 1% Polyethylene Glycol (PEG) of molecular weight 8000 and 0.1% Tween 20. This buffer is used as a diluent for the conjugates.

Antibodies
1. Anti-Alpha, designated INN-132. This antibody is used as the capture antibody.
2. Anti-Alpha, designated WSP-2G5. This antibody is against a different epitopic site than the first and will make a sandwich in the presence of alpha chain consisting of the first antibody, the alpha chain and the second antibody. This system will measure both the free alpha chain and the alpha chain which is bound to beta chain. This second anti-alpha antibody is labelled with an enzyme, Horseradish Peroxidase (HRP) so that detection can be accomplished visually with the addition of a substrate or chromogen that will change color in the presence of HRP.

Plates

Immulon II 96 well polystyrene plates (Dynatech) are used for coating the capture antibody. The capture antibody is diluted in 0.05M Phosphate Buffered Saline (PBS) to a concentration of 10 μg/mL. 100 μL is added per well and incubated overnight. The wells are decanted and then filled with a solution of 0.1M Tris, pH 8.0 containing 2% BSA and 20% sucrose to block any remaining binding sites on the plastic wells. The blocking solution is incubated for a minimum of 30 minutes after which time the plate is decanted and rinsed with tap water. The plate is now ready for use.

Standards

For the total alpha assay, either purified alpha chain or purified intact LH can be used. Both are purchased from Scripps Laboratories, San Diego, Calif. The concentrations used are expressed in Molarity and range from 250 pM to 15.5 pM. Using these standards in an assay allows us to develop a standard curve from which unknown samples can be interpolated.

Tetramethylbenzidine (TMB) Substrate

TMB substrate is prepared using two solutions. The first, TMB solution, is prepared by adding 4.75 g of tetramethylbenzidine to 3.8 L of methanol. This solution should be protected from light. The second solution is substrate buffer with stannate and is prepared by admixing 5.35 g citric acid, 75.27 g sodium phosphate dibasic, 0.31 g sodium stannate, 5.2 mL 30% hydrogen peroxide and 0.26 g thimerosal in sufficient purified water to bring the total volume to 5.2 L. Final pH should be 4.9 to 5.1. This solution should never come in contact with metal. For use, 3 parts of the TMB solution is mixed with 7 parts of the substrate buffer.

Assay Format

50 μL of standard or diluted unknown urine is added in duplicate to wells. 50 μL of diluted anti-alpha conjugated to HRP is added to each test well. Incubation is for one hour at room temperature. The wells are then decanted and washed with tap water to remove any unbound labelled antibody. 100 μL of the chromogen substrate is then added. In the presence of HRP the clear substrate solution will change to a blue color. The amount of bound HRP labelled antibody is proportional to the concentration of alpha chain present in either the standard or the unknown sample and therefore the color generated is in direct proportion to the alpha concentration. The intensity of the color solution is detected by a spectrophotometric plate reader at absorbance 630. A standard curve is drawn (FIG. 2) based on the average of the absorbance values (Table II) and the total alpha chain content of unknown samples is determined by interpolation from the standard curve and the pM multiplied by the dilution factor (Table III).

TABLE II

| TOTAL ALPHA ASSAY STANDARDS | | |
| --- | --- | --- |
| [LH] pM | Absorbance 630 | Average Absorbance Value |
| 0.0 | 0.037 | |
|  | .015 | .026 |
| 15.5 | .071 | |
|  | .056 | .064 |
| 31.0 | .110 | |

TABLE II-continued

TOTAL ALPHA ASSAY STANDARDS

| [LH] pM | Absorbance 630 | Average Absorbance Value |
|---|---|---|
| 62.5 | .108 | .109 |
|  | .206 |  |
| 125.0 | .206 | .206 |
|  | .407 |  |
|  | .448 | .427 |
| 188.0 | .694 |  |
|  | .619 | .656 |
| 250.0 | .964 |  |
|  | .952 | .958 |

TABLE III

UNKNOWNS

| Cycle Day | Dilution Facton | Absorbance 630 | Average Absorbance Value | pM |
|---|---|---|---|---|
| 2 | 2 | .113 |  |  |
|  |  | .107 | .101 | 61 |
| 3 | 2 | .431 |  |  |
|  |  | .451 | .472 | 264 |
| 4 | 2 | .280 |  |  |
|  |  | .240 | .216 | 149 |
| 5 | 2 | .201 |  |  |
|  |  | .218 | .209 | 127 |
| 6 | 2 | .164 |  |  |
|  |  | .188 | .176 | 106 |
| 7 | 2 | .153 |  |  |
|  |  | .136 | .144 | 85 |
| 8 | 2 | .389 |  |  |
|  |  | .340 | .364 | 214 |
| 9 | 2 | .147 |  |  |
|  |  | .149 | .148 | 88 |
| 10 | 2 | .465 |  |  |
|  |  | .362 | .413 | 242 |
| 11 | 2 | 1.780 |  |  |
|  |  | 1.918 | 1.840 | > linear |
| 11 | 8 | .669 |  |  |
|  |  | .627 | .648 | 1490 |
| 11 | 16 | .315 |  |  |
|  |  | .332 | .323 | 1530 |
| 12 | 2 | .666 |  |  |
|  |  | .730 | .698 | 397 |
| 13 | 2 | .253 |  |  |
|  |  | .275 | .264 | 150 |
| 14 | 2 | .273 |  |  |
|  |  | .343 | .308 | 183 |
| 15 | 2 | .166 |  |  |
|  |  | .170 | .168 | 101 |
| 16 | 2 | .179 |  |  |
|  |  | .178 | .178 | 108 |
| 17 | 2 | .191 |  |  |
|  |  | .218 | .204 | 124 |
| 18 | 2 | .107 |  |  |
|  |  | .114 | .110 | 63 |
| 19 | 2 | .100 |  |  |
|  |  | .100 | .100 | 43 |
| 20 | 2 | .184 |  |  |
|  |  | .161 | .172 | 104 |
| 21 | 2 | .184 |  |  |
|  |  | .162 | .173 | 104 |
| 22 | 2 | .117 |  |  |
|  |  | .102 | .109 | 62 |
| 23 | 2 | .139 |  |  |
|  |  | .144 | .141 | 83 |
| 24 | 2 | .342 |  |  |
|  |  | .390 | .366 | 215 |

The foregoing data is plotted in graphical form in FIG. 3 where it can be seen that the total alpha chain surge indicating the fertile period at day 11 is substantial.

We claim:

1. In an assay procedure for determining preovulatory surging of luteinizing hormone, the steps of obtaining a plurality of samples of urine from a host and comparing the total gonadotropal alpha peptide chain content in said samples.

2. An assay procedure for predicting the onset of ovulation in a human subject comprising obtaining a urine sample from a host on each of a plurality of consecutive time periods, analyzing each of said samples to determine total gonadotropal alpha peptide chain content thereof and observing a surge in said total gonadotropal alpha peptide chain content as a prelude to ovulation.

3. An assay procedure as set forth in claim 2, wherein the samples are analyzed using an immunological procedure.

4. An assay procedure as set forth in claim 3, wherein said immunological procedure includes the step of forming a sandwich using two different antibodies, each of said antibodies being specifically bindable to a respective different binding site on said alpha chain.

5. An assay procedure as set forth in claim 4, wherein said immunological procedure comprises a sandwich ELISA procedure.

6. An assay procedure as set forth in claim 2, wherein said consecutive time periods are days and said urine samples are first morning urine samples.

7. An assay procedure as set forth in claim 5, wherein said consecutive time periods are days and said urine samples are first morning urine samples.

* * * * *